United States Patent [19]

Matsuura et al.

[11] Patent Number: 5,329,043
[45] Date of Patent: Jul. 12, 1994

[54] METHOD OF PREPARING METHACROLEIN AND/OR METHACRYLIC ACID

[75] Inventors: Ikuya Matsuura, Toyama; Yukio Aoki, Hyogo, both of Japan

[73] Assignee: Nippon Shokubai Co., Ltd., Osaka, Japan

[21] Appl. No.: 67,067

[22] Filed: May 26, 1993

[30] Foreign Application Priority Data

May 29, 1992 [JP] Japan .................. 4-138615

[51] Int. Cl.$^5$ .............................. C07C 51/16
[52] U.S. Cl. .................... 562/534; 562/532; 562/535; 502/209
[58] Field of Search ............ 562/532, 534, 535, 545; 502/205, 212, 215, 302, 209

[56] References Cited

U.S. PATENT DOCUMENTS 5,153,162 10/1992 Kurimoto et al. .............. 502/209
5,239,115 8/1993 Matsuura ....................... 562/535

FOREIGN PATENT DOCUMENTS 42034 of 1990 Japan .
20237 of 1991 Japan .
106839 of 1991 Japan .

Primary Examiner—Arthur C. Prescott
Attorney, Agent, or Firm—Sherman and Shalloway

[57] ABSTRACT

A method of preparing methacrolein and/or methacrylic acid by catalytic gas phase oxidation of isobutane in the presence of a catalyst, wherein said catalyst is a catalyst containing divanadyl pyrophosphate and represented by general formula (1)

$$P_a V_b X_c Y_d Z_e O_x \qquad (1)$$

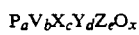

wherein P, V, and O represent phosphorus, vanadium and oxygen, respectively; X represents at least one element selected from the group consisting of cobalt and nickel; Y represents at least one element selected from the group consisting of niobium, tantalum, manganese, iron, copper, zinc, lanthanum, neodymium, samarium, cerium, zirconium, chromium, magnesium, tungsten, tin, hafnium, uranium, indium, cadmium, molybdenum, antimony, bismuth, rhodium, silver and sulfur; Z represents at least one element selected from the group consisting of potassium, rubidium, cesium and thallium; a, b, c, d, e, and x represent atomic ratios, respectively, provided that when a is 1, b is 0.2 to 2, c is 0.01 to 5, d is 0 to 5, and e is 0 to 2, and x represents number of oxygen atoms necessary for satisfying atomic valences of respective component elements.

16 Claims, No Drawings

METHOD OF PREPARING METHACROLEIN AND/OR METHACRYLIC ACID

This invention relates to a method of preparing methacrolein and/or methacrylic acid by catalytic gas phase oxidation of isobutane with molecular oxygen.

Many proposals have hitherto been made for the preparation of methacrolein and/or methacrylic acid using unsaturated hydrocarbons such as isobutene, and tertiary alcohols such as tert-butanol as a starting material, and they have been applied industrially. However, not many proposals have been made for the preparation of methacrolein and/or methacrylic acid using isobutane as a starting material by catalytic gas phase oxidation since isobutane, which is a saturated hydrocarbon, is less reactive. Among the proposals, a method is disclosed in which methacrolein and/or methacrylic acid are/is prepared by catalytic gas phase oxidation of isobutane as a starting material using a catalyst containing a heteropolyacid salt containing as an essential component molybdenum, phosphorus, alkali metals, vanadium or arsenic (Japanese Patent Application Laid-Open No. 106839/1991). Also, a method is disclosed in which methacrolein and/or methacrylic acid are/is prepared by catalytic gas phase oxidation of isobutane using a catalyst containing phosphorus, vanadium, antimony and copper as an essential components (Japanese Patent Application Laid-Open No. 20237/1991). Further, a method is disclosed in which methacrolein and/or methacrylic acid are/is prepared by catalytic gas phase oxidation of isobutane as a starting material using a catalyst containing a silver, zinc, niobium, tantalum, tungsten, manganese, iron or the like salt of a heteropolyacid which contains molybdenum in addition to phosphorus or arsenic as a central element (Japanese Patent Application Laid-Open No. 42034/1990). However, these conventional methods showed low productivities, and therefore, improvement has been desired.

An object of this invention is to provide a method of preparing methacrolein and/or methacrylic acid from isobutane advantageously.

As a result of extensive investigation on catalyst with which methacrolein and/or methacrylic acid can be prepared advantageously by catalytic gas phase oxidation of isobutane as a starting material, a catalyst has now been found that has activity and selectivity high enough to be used practically. This invention is based on this discovery.

Therefore, according to this invention, there is provided a method of preparing methacrolein and/or methacrylic acid by catalytic gas phase oxidation of isobutane in the presence of a catalyst, wherein said catalyst is a catalyst containing divanadyl pyrophosphate and represented by general formula (1)

$$P_a V_b X_c Y_d Z_e O_x \quad (1)$$

wherein P, V, and O represent phosphorus, vanadium and oxygen, respectively; X represents at least one element selected from the group consisting of cobalt and nickel; Y represents at least one element selected from the group consisting of niobium, tantalum, manganese, iron, copper, zinc, lanthanum, neodymium, samarium, cerium, zirconium, chromium, magnesium, tungsten, tin, hafnium, uranium, indium, cadmium, molybdenum, antimony, bismuth, rhodium, silver and sulfur; Z represents at least one element selected from the group consisting of potassium, rubidium, cesium and thallium; a, b, c, d, e, and x represent atomic ratios, respectively, provided that when a is 1, b is 0.2 to 2, c is 0.01 to 5, d is 0 to 5, and e is 0 to 2, and x represents number of oxygen atoms necessary for satisfying atomic valences of respective component elements.

According to the method of this invention, methacrolein and/or methacrylic acid can be prepared from isobutane with high selectivity and high productivity. The reason for such an excellent effect is ascribable to the fact that the catalyst contains divanadyl pyrophosphate in its basic structure. It is reported that divanadyl pyrophosphate is the active component of a catalyst for the synthesis of maleic anhydride by oxidation of butane (G. Busuka et al., Appl. Catal., 25, 264 (1986), and T. Simoda et al., Bull. Chem. Soc. Jpn., 58, 2163 (1985)). Also, it is reported in S. J. Puttocck and C. H. Rochester, J. Chem. Soc., Faraday Trans., 1, 82, 2773 (1986), that divanadyl pyrophosphate has a strong acid site, which activates butane. That is, it considered that the hydrogen atom at the -position of isobutane is readily withdrawn by the strong acid site of divanadyl pyrophosphate, a structural element of the catalyst used in this invention, to liberate a hydrogen radical, thus activating the isobutane, which is then oxidized to produce mainly methacrolein.

The catalyst of this invention contains divanadyl pyrophosphate as an active component. This is confirmed by X ray diffraction analysis as a result of which there are observed a peak in d value (lattice spacing) with d taking various values of about 4.04 Å, 3.90 Å, 3.14 Å, 3.03 Å, 2.66 Å, and 2.44 Å, that is characteristic to divanadyl pyrophosphate ($(VO)_2P_2O_7$).

The catalyst of this invention also contains cobalt or nickel as an essential component. These elements are considered to contribute to increasing the strength of acid site of divanadyl pyrophosphate or increasing oxidizing power of divanadyl pyrophosphate.

The catalyst of this invention may further contain other elements to exhibit more excellent catalyst performances. That is, the catalysts represented by general formula (1) above in which Y represents at least one element selected from the group consisting of niobium, tantalum, cerium, samarium, neodymium, and molybdenum, and d is 0.01 to 5, the catalysts represented by general formula (1) in which Y represents niobium, tantalum or molybdenum, and d is 0.01 to 2, or the catalysts represented by general formula (1) in which Z represents at least one element selected from the group consisting of potassium, rubidium, cesium, and thallium, and e is 0,001 to 2, exhibit particularly excellent performances. However, if the catalysts contain Y or Z components more than is prescribed by d or e above have decreased catalyst performances.

The vanadium atom in divanadyl pyrophosphate has a valence of 4. On the other hand, it is observed that the catalyst containing divanadyl pyrophosphate as an active component and represented by general formula (1), and a part of the vanadium atoms therein is a pentavalent vanadium atom, has much more increased catalyst activity. Catalysts are preferred in which pentavalent vanadium atom is present in an amount of 1 to 90% based on total vanadium atoms in the catalyst. Such a catalyst can be obtained, for example, by using divanadyl pyrophosphate and pentavalent vanadium atom such as vanadyl phosphate in combination. However, the catalyst additionally containing pentavalent vanadium atom can also be obtained with ease by heating divanadyl pyrophosphate at 200° to 700° C. in an oxygen-containing atmosphere gas to oxidize a portion of tetravalent vanadium atoms into pentavalent vanadium atom. As described above, the catalyst of which a portion of tetravalent vanadium atoms is oxidized and converted into pentavalent vanadium atom has a particularly high catalytic activity and therefore desirable. Ratio of generation of pentavalent vanadium atoms can be controlled by varying concentration (partial pressure) of oxygen in the atmosphere in which oxidation treatment is performed, temperature of the treatment, time of the treatment and so on.

Presence or absence of pentavalent vanadium atoms can be detected by X ray diffraction analysis. If present, there can be observed a peak in d value with d taking various values of about 4.88 Å, 4.23 Å, 3.20 Å, 2.68 Å, and 2.44 Å, or at about 4.72 Å, 4.12 Å, 3.15 Å, 2.65 Å, and 2.56 Å. The amount of pentavalent vanadium in the catalyst can be determined quantitatively by titration method with ammonium iron (II) sulfate.

Catalyst containing divanadyl pyrophosphate, and a heteropolyacid containing phosphorus and molybdenum, and/or its salts, simultaneously are very interesting. That is, catalysts which contain divanadyl pyrophosphate as an active component, and are represented by general formula (1), in which a portion of phosphorus atoms is contained in the form of a heteropolyacid and/or its salts, have strong acidity and oxidizing power. Use of such a catalyst can give rise to conversion of isobutane, selectivity of methacrylein or methacrylic acid higher than are obtained by using only the catalyst represented by general formula (1) containing divanadyl pyrophosphate as an active component, or using only a heteropolyacid acid/or its salts containing phosphorus and molybdenum. In this type of catalyst, the proportion of the amount of phosphorus in the heteropolyacid and/or its salts to the amount of total phosphorus in the catalyst is preferably 1 to 50%, and more preferably 5 to 40%.

Various methods can be used for the preparation of the catalyst of this invention. For example, a vanadium compound such as vanadium pentoxide is reduced, and then reacted with a phosphorus compound such as orthophosphoric acid to prepare $VOHPO_4 \cdot 0.5H_2O$ (X ray diffraction analysis confirmed d values of about 5.72 Å, 4.54 Å, 3.58 Å, 3.30 Å, 3.12 Å, and 2.94 Å, showing a peak of d value). This is heat-treated in an inert gas such as nitrogen or helium at a temperature within the range of 300° to 700° C. to obtain the objective catalyst. As the method for reducing the vanadium compound, there can be applied various methods including a method in which a vanadium compound is reduced in an aqueous solvent with a reducing agent such as hydrogen chloride, a method in which a vanadium compound is reduced in an organic solvent having a reducing ability, combination of these methods, etc. In the case where a catalyst is to be prepared which contains cobalt, nickel, niobium, manganese, iron, or the like, the aforementioned metal salts, for example, chlorides, sulfates, nitrates, ammonium salts, carbonates, hydroxides, oxides, etc. are added to the reduced vanadium compound together with orthophosphoric acid, and allowed to react. Then, the resultant $VOHPO_4 \cdot 0.5H_2O$ is heat-treated in an inert gas to obtain the objective catalyst.

As the phosphorus source used for preparing the catalyst, there can be cited, for example, pentavalent phosphorus compounds such as orthophosphoric acid, pyrophosphoric acid, phosphorus pentoxide, phosphorus pentachloride, and sodium phosphate. As the reducing agent for pentavalent vanadium compounds, there can be applied ordinary reducing agents such as hydrogen chloride, hydroxylamine chloride, hydrazines, aliphatic and aromatic alcohols having 1 to 6 carbon atoms, etc. These catalysts can be used as carried on a carrier or after being diluted with a carrier. Examples of the carrier include silica, alumina, silicon carbide, titania, titania-silica, zirconia, zeolite, etc. Shape of the catalyst is not limited particularly and may be cylindrical, spherical, ring-shaped, or the like.

Raw material gas for preparing methacrolein and/or methacrylic acid from isobutane is preferably a mixed gas containing 10 to 80% by volume of isobutane and oxygen in an oxygen-to-isobutane proportion of 0.1 to 3. The raw material gas may contain water vapor or may be without water vapor. If it contains water vapor, it is preferred that molar proportion of water vapor to isobutane be within the range of 0.1 to 3. Further, the aforementioned mixed gas may be diluted with an inert gas such as nitrogen, carbon dioxide, or helium. The reaction temperature is preferably within the range of 200° to 400° C., and the reaction pressure is preferably within the range of from atmospheric pressure to 30 kg/cm².

Next, this invention will be described concretely by non-limitative Examples.

EXAMPLE 1

To 80 ml of isobutyl alcohol heated to about 80° C. was added 10 g of vanadium pentoxide, and hydrogen chloride gas was passed through the mixture for 5 minutes with stirring. To this was added a mixture of 12.4 g of 98% by weight orthophosphoric acid and 2.7 g of cobalt chloride, and the resultant mixture was refluxed for 1 hour. Then, 100 ml of toluene was added thereto and the mixture was heated to remove isobutyl alcohol. The precipitates which formed in the toluene were filtered, and dried at about 120° C. Upon X ray diffraction analysis, the solid thus obtained showed d values of 5.72 Å, 4.54 Å, 3.58 Å, 3.12 Å, and 2.94 Å, thus showing a peak in d value which is characteristic to $VOHPO_4 \cdot 0.5H_2O$. The solid was heated at 500° C. for 8 hours in helium gas, and then ground to 24 to 35 mesh to obtain a catalyst of this invention.

The catalyst thus prepared had a composition of $P_1V_{0.9}Co_{0.09}O_x$. Upon X ray diffraction analysis, this showed d values of 4.04 Å, 3.90 Å, 3.14 Å, 3.02 Å, 2.66 Å, 2.43 Å, and 2.10 Å, thus showing a peak in d value, which confirmed that the catalyst has a structure of $(VO)_2P_2O_7$.

In a reaction tube filled with 3 g of the aforementioned catalyst was passed a mixed gas having a composition and flow rate of 30 ml/min of isobutane, 15 ml/min of oxygen, and 15 ml/min of water vapor, and heated for oxidation reaction. As a result, at a reaction temperature of 280° C., conversion of isobutane was 13.9%, and selectivities of methacrolein and methacrylic acid were 22% and 32%, respectively. Selectivity of isobutene was 0.5%. As by-products, acetone and propylene were detected.

EXAMPLE 2

A catalyst of this invention was prepared in the same manner as in Example 1 except that 2.7 g of nickel chloride was used instead of cobalt chloride.

The catalyst prepared had a composition of $P_1V_{0.9}Ni_{0.09}O_x$. X Ray diffraction analysis confirmed that the catalyst has a structure of mainly $(VO)_2P_2O_7$.

Catalyst performance test on oxidation of isobutane was conducted in the same manner as in Example 1 using this catalyst, and as a result, conversion of isobutane was 11.8%, and selectivities of methacrolein and methacrylic acid were 24% and 24%, respectively.

EXAMPLE 3

A catalyst of this invention was prepared in the same manner as in Example 1 except that a mixture of 12.4 g of 98% by weight orthophosphoric acid, 2.7 g of cobalt chloride, and 10.1 g of niobium pentachloride was used instead of a mixture of 98% by weight orthophosphoric acid and cobalt chloride.

The catalyst prepared had a composition of $P_1V_{0.9}Co_{0.09}Nb_{0.3}O_2$. X Ray diffraction analysis confirmed that the catalyst has a structure of mainly $(VO)_2P_2O_7$.

Catalyst performance test on oxidation of isobutane was conducted in the same manner as in Example 1 using this catalyst, and as a result, conversion of isobutane was 23.6%, and selectivities of methacrolein and methacrylic acid were 45.2% and 21.7%, respectively.

EXAMPLE 4

A catalyst of this invention was prepared in the same manner as in Example 1 except that a mixture of 12.4 g of 98% by weight orthophosphoric acid, 2.7 g of nickel chloride, and 17.8 g of tantalum pentachloride was used instead of a mixture of 98% by weight orthophosphoric acid and cobalt chloride. The catalyst prepared had a composition of $P_1V_{0.9}Ni_{0.09}Ta_{0.4}O_x$. X Ray diffraction analysis confirmed that the catalyst has a structure of mainly $(VO)_2P_2O_7$.

Catalyst performance test on oxidation of isobutane was conducted in the same manner as in Example 1 using catalyst, and as a result, conversion of isobutane was 21.2%, and selectivities of methacrolein and methacrylic acid were 36.5% and 28.5%, respectively.

EXAMPLE 5

A catalyst of this invention was prepared in the same manner as in Example 1 except that 9.2 g of cerium chloride was used instead of cobalt chloride.

The catalyst prepared had a composition of $P_1V_{0.9}Ce_{0.2}O_x$. X Ray diffraction analysis confirmed that the catalyst has a structure of mainly $(VO)_2P_2O_7$.

Catalyst performance test on oxidation of isobutane was conducted in the same manner as in Example 1 using this catalyst, and as a result, conversion of isobutane was 19.7%, and selectivities of methacrolein and methacrylic acid were 31.2% and 32%, respectively.

EXAMPLE 6

A catalyst of this invention was prepared in the same manner as in Example 1 except that a mixture obtained by adding 3.0 g of iron chloride and 2.2 g of manganese chloride to the 98% by weight orthophosphoric acid and cobalt chloride was used instead of a mixture of 98% by weight orthophosphoric acid and cobalt chloride.

The catalyst prepared had a composition of $P_1V_{0.9}Co_{0.09}Fe_{0.09}Mn_{0.09}O_x$. X Ray diffraction analysis confirmed that the catalyst has a structure of mainly $(VO)_2P_2O_7$.

Catalyst performance test on oxidation of isobutane was conducted in the same manner as in Example 1 using this catalyst, and as a result, conversion of isobutane was 17.9%, and selectivities of methacrolein and methacrylic acid were 52.6% and 18.6%, respectively.

EXAMPLE 7

A catalyst of this invention was prepared in the same manner as in Example 2 except that a mixture obtained by adding 1.9 g of copper chloride and 1.5 g of zinc chloride to the 98% by weight orthophosphoric acid and cobalt chloride was used instead of a mixture of 98% by weight orthophosphoric acid and cobalt chloride.

The catalyst prepared had a composition of $P_1V_{0.9}Ni_{0.09}Cu_{0.09}Zn_{0.09}O_x$. X Ray diffraction analysis confirmed that the catalyst has a structure of mainly $(VO)_2P_2O_7$.

Catalyst performance test on oxidation of isobutane was conducted in the same manner as in Example 1 using this catalyst, and as a result, conversion of isobutane was 16.8%, and selectivities of methacrolein and methacrylic acid were 50.7% and 21.0%, respectively.

EXAMPLES 8 TO 16

Catalysts of this invention having compositions shown in Table 1 were prepared similarly to Example 1. X Ray diffraction analysis confirmed that the catalysts each have a structure of mainly $(VO)_2P_2O_7$.

Catalyst performance tests on oxidation of isobutane were conducted in the same manner as in Example 1 at reaction temperatures shown in Table 1. Using this catalyst, and as results shown in Table were obtained.

EXAMPLE 17

In 100 g of deionized water were dissolved 30 g of ammonium molybdenate, and 1.66 g of ammonium metavanadate with heating. To the solution were added 1.63 g of 85% orthophosphoric acid, and further 4.14 g of cesium nitrate dissolved in 30 g of deionized water, followed by adjusting pH to below 1 with concentrated nitric acid, and the resulting slurry was aged at 95° C. for 1 hour. Then, the slurry was concentrated to dryness while heating at 100° C. with stirring. The solid obtained was heated at 350° C. in the air. X Ray diffraction analysis confirmed that the solid thus obtained has a heteropolyacid structure consisting of phosphorus and molybdenum. A portion (20 g) of the solid was ground, and ground product of $VOHPO_4$ $0.5H_2O$ was mixed therewith. The mixture was kneaded with a small amount of water, molded, dried at 120° C., heated at 500° C. for 8 hours in helium gas, and then ground to 24 to 35 mesh to obtain a catalyst of this invention.

X Ray diffraction analysis confirmed that the catalyst has a peak characteristic to $(VO)_2P_2O_7$ structure and a peak characteristic to a Keggin structure consisting of phosphorus and molybdenum.

Catalyst performance test on oxidation of isobutane was performed using 3 g of this catalyst according to the method in Example 1. As a result, conversion of isobutane was 20.1%, and selectivities of methacrolein and methacrylic acid were 37.2% and 32.6%, respectively.

EXAMPLE 18

A catalyst of this invention was prepared in the same manner as in Example 1 except that after heating at 500° C. for 8 hours in helium gas, the solid was further heated at 600° C. for 3 hours in the air before it was ground to 24 to 35 mesh.

Upon X ray diffraction analysis, it was confirmed that the catalyst has a peak of divanadyl pyrophosphate, and there were observed d values of 4.72 Å, 4.12 Å, 3.15 Å, 2.65 Å, and 2.56 Å, thus showing a peak in d value. In addition, presence of pentavalent vanadium atom was confirmed. Determination of pentavalent vanadium revealed that the proportion of the amount of pentavalent vanadium atoms to the amount of total vanadium atoms in the catalyst was 55%.

Catalyst performance test on oxidation of isobutane was performed using 3 g of this catalyst according to the method in Example 1. As a result, at a reaction temperature of 280° C., conversion of isobutane was 15.2%, and selectivities of methacrolein acid were 19.5% and 34.2%, respectively.

COMPARATIVE EXAMPLE 1

A catalyst for comparison was prepared in the same manner as in Example 1 except that only 12.4 g of 98% by weight orthophosphoric acid was used instead of a mixture of 98% by weight orthophosphoric acid and cobalt chloride.

The catalyst prepared had a composition of $P_1V_{0.9}O_x$. X Ray diffraction analysis confirmed that the catalyst has a structure of mainly $(VO)_2P_2O_7$.

Catalyst performance test on oxidation of isobutane was conducted in the same manner as in Example 1 using 3 g of this catalyst, and as a result, at a reaction temperature of 280° C., conversion of isobutane was 1.6%, and selectivities of methacrolein and methacrylic acid were 56.6% and 2.1%, respectively.

the group consisting of niobium, tantalum, manganese, iron, copper, zinc, lanthanum, neodymium, samarium, cerium, zirconium, chromium, magnesium, tungsten, tin, hafnium, uranium, indium, cadmium, molybdenum, antimony, bismuth, rhodium, silver and sulfur; Z represents at least one element selected from the group consisting of potassium, rubidium, cesium and thallium; a, b, c, d, e, and x represent atomic ratios, respectively, provided that when a is 1, b is 0.2 to 2, c is 0.01 to 5, d is 0 to 5, and e is 0 to 2, and x represents number of oxygen atoms necessary for satisfying atomic valences of respective component elements.

2. The method of claim 1, wherein said catalyst is a catalyst represented by general formula (1) above wherein Y represents niobium, tantalum, cerium, samarium, neodymium, or molybdenum; and d is 0.01 to 5.

3. The method of claim 1, wherein said catalyst is a catalyst represented by general formula (1) above wherein Y represents niobium, tantalum, or molybdenum; and d is 0.01 to 2.

4. The method of claim 1, wherein said catalyst is a catalyst represented by general formula (1) above wherein Z represents potassium, rubidium, cesium or thallium; and e is 0,001 to 2.

5. The method of claim 1, wherein said catalyst is a catalyst of which a portion of vanadium atoms contained is a pentavalent vanadium atom.

6. The method of claim 5, wherein amount of said pentavalent vanadium atom is 1 to 90% of total vanadium atoms contained in said catalyst.

7. A method of preparing methacrolein and/or methacrylic acid by catalyst gas phase oxidation of isobutane which comprises contacting the isobutane with a cata-

TABLE 1

| Example | Catalyst Composition (Atomic Ratio Excepting O) | Reaction Temperature (°C.) | Conversion of Isobutane (%) | Selectivity (%) Methacrolein | Methacrylic Acid |
|---|---|---|---|---|---|
| 1 | $P_1V_{0.9}Co_{0.09}$ | 280 | 13.9 | 22 | 32 |
| 2 | $P_1V_{0.9}Ni_{0.09}$ | 280 | 11.8 | 24 | 24 |
| 3 | $P_1V_{0.9}Co_{0.09}Nb_{0.3}$ | 280 | 23.6 | 45.2 | 21.7 |
| 4 | $P_1V_{0.9}Ni_{0.09}Ta_{0.4}$ | 280 | 21.2 | 36.5 | 28.5 |
| 5 | $P_1V_{0.9}Co_{0.09}Ce_{0.2}$ | 280 | 19.7 | 31.2 | 32 |
| 6 | $P_1V_{0.9}Co_{0.09}Fe_{0.09}Mn_{0.09}$ | 300 | 17.9 | 52.6 | 18.6 |
| 7 | $P_1V_{0.9}Ni_{0.09}Cu_{0.09}Zn_{0.09}$ | 350 | 16.8 | 50.7 | 21.0 |
| 8 | $P_1V_{0.9}Co_{0.2}La_{0.05}Zr_{0.05}$ | 290 | 15.1 | 51.3 | 19.5 |
| 9 | $P_1V_{0.9}Co_{0.2}Sm_{0.05}Cr_{0.02}Ta_{0.02}Mg_{0.01}$ | 290 | 15.9 | 49.3 | 17.1 |
| 10 | $P_1V_{0.9}Co_{0.1}W_{0.01}Sn_{0.01}Bi_{0.01}$ | 300 | 16.2 | 49.5 | 16.5 |
| 11 | $P_1V_{0.9}Co_{0.1}In_{0.01}Sb_{0.01}Ag_{0.01}$ | 300 | 15.3 | 43.6 | 18.2 |
| 12 | $P_1V_{0.9}Ni_{0.1}Nd_{0.01}Cd_{0.01}Mo_{0.2}$ | 310 | 14.9 | 41.2 | 21.7 |
| 13 | $P_1V_{0.9}Ni_{0.1}Hf_{0.1}S_{0.1}Rh_{0.01}$ | 300 | 16.5 | 52.5 | 20.6 |
| 14 | $P_1V_{0.9}Co_{0.09}Nb_{0.2}K_{0.01}$ | 330 | 10.9 | 50.2 | 15.1 |
| 15 | $P_1V_{0.9}Co_{0.09}Nb_{0.2}Rb_{0.01}Cs_{0.01}$ | 330 | 11.5 | 49.8 | 14.9 |
| 16 | $P_1V_{0.9}Co_{0.09}Ta_{0.1}Tl_{0.1}$ | 330 | 10.6 | 49.8 | 13.1 |
| 17 | $P_1V_{0.9}Co_{0.09} + P_1Mo_{12}V_1Cs_{1.5}$ | 280 | 20.1 | 37.2 | 32.6 |
| 18 | $P_1V_{0.9}Co_{0.09}$ | 280 | 15.2 | 19.5 | 34.6 |
| C.E.1 | $P_1V_{0.9}$ | 280 | 1.6 | 56.6 | 2.1 |

What is claimed is:

1. A method of preparing methacrolein and/or methacrylic acid by catalyst gas phase oxidation of isobutane in the presence of a catalyst, wherein said catalyst is a catalyst containing divanadyl pyrophosphate and represented by general formula ( 1 )

$$P_aV_bX_cY_dZ_eO_x \qquad (1)$$

wherein P, V, and O represent phosphorus, vanadium and oxygen, respectively; X represents at least one element selected from the group consisting of cobalt and nickel; Y represents at least one element selected from lyst containing divanadyl pyrophosphate and represented by the general formula (2)

$$P_aV_bX_cO_x \qquad (21)$$

wherein P, V, and O represent phosphorus, vanadium and oxygen, respectively; X represents at least one element selected from the group consisting of cobalt and nickel; a, b, c and x represent atomic ratios, respectively, provided that when a is 1, b is 0.2 to 2, c is 0.01 to 5, and x represents number of oxygen atoms necessary for satisfying atomic valences of respective component elements.

8. The method of claim 7, wherein said catalyst is a catalyst represented by general formula (2) above and further contains at least one of niobium, tantalum, cerium, samarium, neodymium, or molybdenum and d is 0.01 to 5.

9. The method of claim 8, wherein said catalyst is a catalyst represented by general formula (1) above and further contains at least one of potassium, rubidium, cesium or thallium and e is 0.001 to 2.

10. The method of claim 7, wherein said catlayst contains pentavalent vanadium atoms in an amount of 1 to 90% of the total vanadium atoms contained in said catalyst.

11. A method of preparing methacrolein and/or methacrylic acid by catalyst gas phase oxidation of isobutane which comprises contacting the isobutane with a catalyst containing divanadyl pyrophosphate and represented by the general formula (1)

$$P_a V_b X_c Y_d Z_e O_x \quad (1)$$

wherein P, V, and O represent phosphorus, vanadium and oxygen, respectively; X represents at least one element selected from the group consisting of cobalt and nickel; Y represents at least one element selected from the group consisting of niobium, tantalum, manganese, iron, copper, zinc, lanthanum, neodymium, samarium, cerium, zirconium, chromium, magnesium, tungsten, tin, hafnium, uranium, indium, cadmium, molybdenum, antimony, bismuth, rhodium, silver and sulfur; Z represents at least one element selected from the group consisting of potassium, rubidium, cesium and thallium; a, b, c, d, e, and x represent atomic ratios, respectively, provided that when a is 1, b is 0.2 to 2, c is 0.01 to 5, d is 0.01 to 5, and e is 0 to 2, and x represents number of oxygen atoms necessary for satisfying atomic valences of respective component elements.

12. The method of claim 11, wherein said catalyst is a catalyst represented by general formula (1) above wherein Y represents niobium, tantalum, cerium, samariuim, neodymium, or molybdenum.

13. The method of claim 12, wherein said catalyst is a catalyst represented by general formula (1) above wherein Y represents niobium, tantalum, or molybdenum; and d is 0.01 to 2.

14. The method of claim 11, wherein said catalyst is a catalyst represented by general formula (1) above wherein Z represents potassium, rubidium, cesium or thallium; and e is 0.001 to 2.

15. The method of claim 13, wherein said catalyst is a catalyst represented by the general formula (1) above wherein Z represents potassium, rubidium, cesium or thallium; and e is 0.001 to 2.

16. The method of claim 11, wherein said catalyst contains pentavalent vanadium atoms in an amount of 1 to 90% of total vanadium atoms contained in said catalyst.

* * * * *